United States Patent
Frister

(10) Patent No.: US 9,504,814 B2
(45) Date of Patent: Nov. 29, 2016

(54) APPARATUS FOR APPLYING A TATTOO OR PERMANENT MAKE-UP

(75) Inventor: Tilo Frister, Berlin (DE)

(73) Assignee: MT DERM GMBH, Berlin (DE)

( * ) Notice: Subject to any disclaimer, the term of this patent is extended or adjusted under 35 U.S.C. 154(b) by 1822 days.

(21) Appl. No.: 10/843,685

(22) Filed: May 12, 2004

(65) Prior Publication Data

US 2005/0010236 A1    Jan. 13, 2005

(30) Foreign Application Priority Data

Jul. 8, 2003  (EP) .................................... 03015403

(51) Int. Cl.
*A61B 17/34*  (2006.01)
*A61M 37/00*  (2006.01)

(52) U.S. Cl.
CPC ...... *A61M 37/0076* (2013.01); *A61M 37/0084* (2013.01)

(58) Field of Classification Search
CPC .................... A61M 37/0076; A61B 17/32002
USPC ................ 606/185, 186, 169, 171; 604/181; 81/9.22
See application file for complete search history.

(56) References Cited

U.S. PATENT DOCUMENTS

| 3,577,579 | A | * | 5/1971 | Duve et al. ..................... 15/22.1 |
| 4,582,060 | A | | 4/1986 | Bailey |
| 4,914,988 | A | * | 4/1990 | Chang ............................. 81/9.22 |
| 5,393,207 | A | * | 2/1995 | Maher et al. ............... 417/423.7 |
| 5,472,449 | A | * | 12/1995 | Chou ............................. 606/186 |
| 5,586,473 | A | * | 12/1996 | Chou ............................. 81/9.22 |
| 5,776,158 | A | | 7/1998 | Chou |
| 6,033,421 | A | * | 3/2000 | Theiss et al. ................. 606/186 |
| 6,345,553 | B1 | | 2/2002 | Adler et al. |
| 6,439,857 | B1 | * | 8/2002 | Koelzer et al. ............ 417/222.1 |
| 2003/0195542 | A1 | * | 10/2003 | Lee ............................... 606/186 |

FOREIGN PATENT DOCUMENTS

| DE | 299 19 199 U | 1/2000 |
| DE | 200 12 369 U | 12/2000 |
| DE | 299 23 931 U | 6/2001 |
| EP | 0 374 355 A | 6/1990 |
| FR | 2 747 928 A1 | 10/1997 |

* cited by examiner

*Primary Examiner* — Diane Yabut
(74) *Attorney, Agent, or Firm* — Leason Ellis LLP

(57) ABSTRACT

The invention relates to an apparatus for applying a tattoo or permanent make-up, comprising a disposable module removably arranged at a handpiece, a needle retained at one end in a needle shaft and supported for movement in a needle guide formed in the disposable module and at another end extending through a needle nozzle opening for discharge of color, and a drive mechanism composed of several structural members and coupled to the needle shaft to effect reciprocating movements of the needle, said plurality of structural members of the drive mechanism comprising drive and coupling means to couple the drive means to the needle shaft. At least part of the coupling means are arranged in the disposable module and removable from the handpiece together with the disposable module.

15 Claims, 3 Drawing Sheets

APPARATUS FOR APPLYING A TATTOO OR PERMANENT MAKE-UP

The invention relates to an apparatus for applying a tattoo or permanent make-up.

As a rule, such apparatus are designed to be handheld and used by operators to apply a color for tattooing or permanent make-up in the area of the surface of skin. A handheld apparatus of this kind is known, for instance, from publication DE 299.19 199.0. The known handheld apparatus comprises a handle, a needle drive means, a needle, and a needle nozzle. Here, at least two modules are provided which are releasably interconnected, at least one of them being designed as a reusable basic module having an integrated needle drive. The other one of the two modules is a sterilized, disposable module integrating all those component parts of the handheld apparatus which might become infected by a customer's body fluids. The handheld apparatus thus is presented in the form of two modules one of which, the disposable one, may be exchanged upon use, while the other one which includes the needle drive means, is used again. The hygienic conditions in applying tattooing or permanent make-up are improved by virtue of the disposable module since all those parts are replaced which potentially may have become infected by body fluid issuing during treatment of a customer. In this way a total exchange of the entire handheld apparatus can be avoided.

It is an object of the invention to provide an improved apparatus having optimized characteristics of use. It is likewise an object of the invention to provide an apparatus for applying a tattoo or permanent make-up with which the exchange of parts subject to wear is facilitated.

These objects are met, in accordance with the invention, by an apparatus as recited in independent claim 1.

In an apparatus for applying a tattoo or permanent make-up, comprising a disposable module removably arranged at a handpiece, a needle retained at one end in a needle shaft and supported for movement in a needle guide formed in the disposable module and, at its other end, extending through a needle nozzle opening, and a drive mechanism composed of several structural members and coupled to the needle shaft to effect reciprocating movements of the needle, said plurality of structural members of the drive mechanism comprising drive and coupling means to couple the drive means to the needle shaft, the invention embodies a concept according to which at least part of the coupling means are arranged in the disposable module and removable from the handpiece together with the disposable module.

It is an essential advantage obtained by the invention over the prior art that when dismantling the disposable module from the handpiece not only those parts of the apparatus can be removed which potentially come into contact with body fluid during treatment but also component parts of the coupling means which are subject to wear.

The drive mechanism not only provides driving motion to move the needle during application of the tattoo or permanent make-up but also introduces the driving motion into the needle shaft through the coupling means. The coupling means are subject to considerable wear because of the high frequency movements of the needle in applying the color. As the coupling means are replaceable, at least in part, due to the module being disposable the frequency of use and, therefore, the service life of the handpiece can be prolonged. Exchanging parts of the coupling means in connection with the disposable module, moreover, permits the exchangeable components to be made of simpler and less costly materials since they are intended only for a limited time of use.

It is provided, in a preferred embodiment of the invention, that the coupling means comprise a conversion mechanism to convert rotary drive motion generated by the drive means into linear motion which is introduced into the needle shaft. Simple and inexpensive models are available of drive means in the form of motors generating rotational movement.

The replacement of used components of the conversion mechanism is facilitated, in a convenient further development of the invention, by the fact that the conversion mechanism is formed partly in the disposable module and removable from the handpiece together with the disposable module.

In an advantageous further development of the invention a mechanism for reliably converting the rotary motion of the drive means into linear motion, with the aid of wear-resistant coupling means, is obtained by the fact that the coupling means comprise a wobble plate secured to the motor and a tappet which is coupled to the needle shaft and runs on the wobbling surface of the wobble plate when the drive means is operating.

In an advantageous embodiment of the invention a torque resistance member comprised by the coupling means is arranged in the disposable module and removable from the handpiece together with the disposable module. The torque resistance member serves to prevent twisting movements of one or more of the component parts of the coupling means when the needle is driven.

The invention will be described further, by way of example, with reference to the accompanying drawing, in which.

Figure 1:
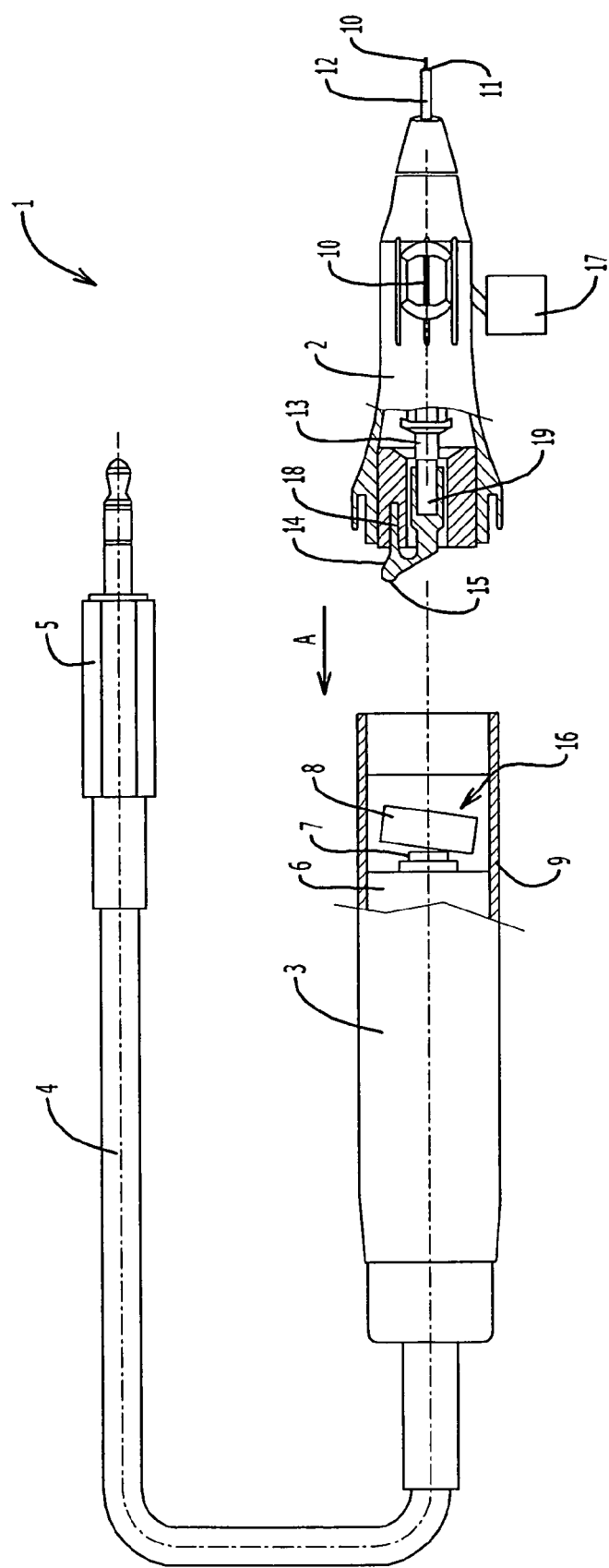
FIG. 1 is a diagrammatic, partly sectional illustration of an apparatus for applying tattooing or permanent make-up.

FIG. 1 is an illustration, partly in section, showing an apparatus 1 for applying tattooing or permanent make-up, comprising a disposable module 2 and a handpiece 3. The handpiece 3 is adapted to be connected to a control device (not shown) by a control line 4 connected to the handpiece 3 and a plug 5 coupled to the control line 4, thus assuring controlled power supply to a motor 6 housed in the handpiece 3. A wobble plate 8 is mounted on a drive shaft 7 of the motor 6 to carry out wobbling movements as the drive shaft 7 rotates. The motor 6 and the wobble plate 8 both are received in a casing 9 of the handpiece 3.

In FIG. 1 the disposable module 2 is shown separated from the handpiece 3 because the disposable module 2 is removable as a whole from the handpiece 3. Removing the disposable module 2, therefore, likewise means taking off from the handpiece 3 a needle 10, which also might be a group of individual needles, extending through a needle nozzle opening 11 and being supported in a needle nozzle 12 which, at the same time, serves as a needle guide, furthermore a needle shaft 13 in which one end of the needle 10 is received, and finally a tappet 14. The needle shaft 13 and the tappet 14 may be made in one piece.

For operation of the apparatus 1, the disposable module 2 is mounted on the handpiece 3 by means of a plug-in or screw connection so that an end 15 of the tappet 14 facing the motor 6 will come to lie on a surface 16 of the wobble plate 8. This mounting of the disposable module 2 on the handpiece 3 is effected by moving it in the direction of arrow A towards the handpiece 3 and then joining the two. Upon rotation of the drive shaft 7 of the motor 6 the end 15 of the tappet 14 is moved back and forth by the wobbling motion of the wobble plate 8. An end member 19 of the needle shaft 13 is coupled to the tappet 14 so that the reciprocating movements of the tappet 14 are transmitted to the needle 10 which thus moves through the needle nozzle opening 11 of the needle nozzle 12. The end 15 of the tappet 14 is pressed against the surface 16 of the wobble plate 8 by suitable retaining means (not shown). They may be embodied, for example, by a mechanical spring conveniently exerting pressure on the needle shaft 13. The wobble plate 8 and the tappet 14 belong to a conversion mechanism by which the rotary motion supplied by the motor 6 through the drive shaft 7 is converted into linear motion. The conversion mechanism itself forms part of coupling means to introduce the drive motion generated by the motor 6 into the needle shaft 13, the coupling means of this embodiment comprising the wobble plate 8, the tappet 14, and the end member 19.

Reciprocating movements of the needle 10 cause a color to be discharged from a reservoir 17 of color matter communicating with the needle nozzle opening 11, as shown diagrammatically in FIG. 1. The way in which the color is discharged, e.g. with or without application of pressure, is not critical to the invention. Various manners of discharging color which are known as such may be applied. For example, the reservoir 17 for the color may be integrated in the disposable module 2 in the form of a cavity, or it may be devised as a cartridge to be attached releasably to the disposable module 2. Moreover, a reservoir 17 for the color may be dispensed with altogether and the job be done by immersing the needle nozzle 12 in a supply of color. In this case the color to be discharged will get into the needle nozzle 12 through capillary action towards a specific space for color, which may be provided in an embodiment, and as the needle 10 moves, when in use, the color will be discharged from the needle nozzle opening 11.

The embodiment of the apparatus 1 illustrated in FIG. 1 permits joint removal from the handpiece 3 of at least the tappet 14, equipped with torque resistance means 18, as a component part of the conversion mechanism which in turn forms part of the coupling means, together with other structural members which potentially may be infected by a customer's body fluid. The latter, as a rule, will be the needle 10, the needle nozzle 12, and possibly the needle shaft 13.

The embodiment illustrated in FIG. 1 of the means to carry out movements of the needle, comprising the wobble plate 8 and the tappet 14, presents just one possibility of implementing such means in apparatus for applying a tattoo or permanent make-up. Those skilled in the art are familiar with other drive mechanisms which typically comprise the drive itself and coupling means for inducing driving motion in the needle shaft. The concept of integrating components of the coupling means in the disposable module can be implemented with other known drive means as well, especially so as to permit replacement of elements which are subjected to increased wear during use together with the exchange of the disposable module.

Figure 2:
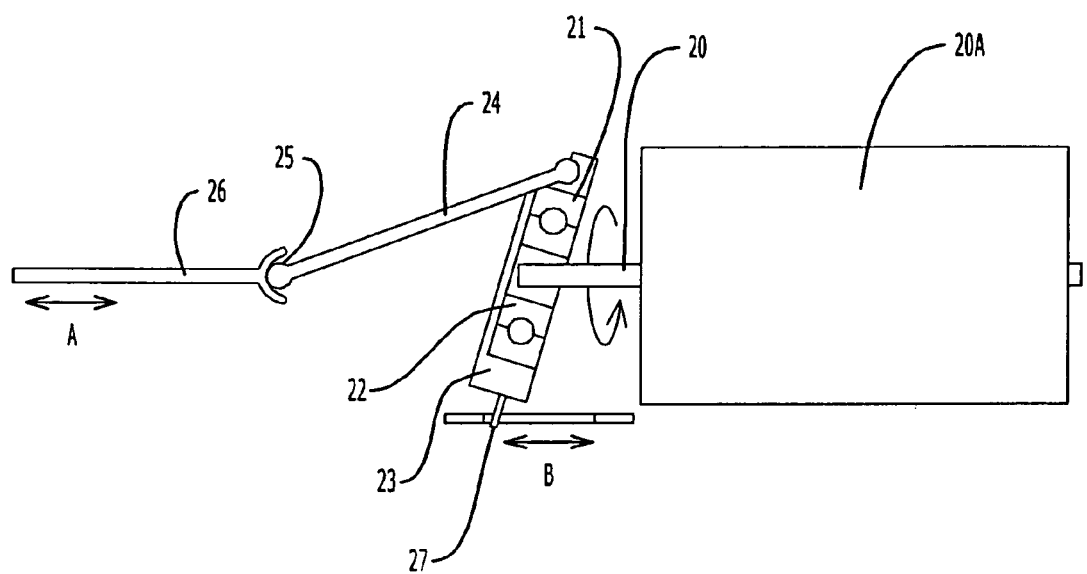
FIG. 2 is a diagrammatic illustration of another drive mechanism for the apparatus shown in FIG. 1.

An example of another drive mechanism for the apparatus 1 is illustrated diagrammatically in FIG. 2. Here, a drive shaft 20 of a motor 20a is shown on which a ball bearing 21 is mounted, including a fixed inner raceway 22 secured at an inclination on the drive shaft 20 and a free-wheeling outer raceway 23. A connecting rod 24, on the one hand, is retained on the outer raceway 23 and, on the other hand, coupled by a joint 25 to a thrust rod 26. Upon rotation of the drive shaft 20, the ball bearing 21 is set into wobbling motion which is converted into linear drive motion in the direction of arrow A by means of the connecting rod 24 and the thrust rod 26 to move the needle shaft. At this time, the outer raceway 23 is held by a torque resistance means 27 which moves back and forth in the direction of arrow B. With this embodiment, the motor 20a and the drive shaft 20 form the drive means, while the remaining structural elements act as coupling members which in turn comprise a conversion mechanism for converting the rotary motion into linear motion.

In a convenient embodiment, the wobble plate 8 of the apparatus 1 as illustrated in FIG. 1 is replaced by the ball bearing 21 with the inner raceway 22 and the outer free-wheeling raceway 23 illustrated in FIG. 2. Twisting of the outer raceway 23 conveniently is prevented by clamping the outer raceway 23 when the disposable module 2 is mounted on the handpiece 3. Alternatively or in addition, a recess (not shown) may be formed in the disposable module 2 to be engaged by the outer raceway 23 or by a projection provided on the same, similar to the torque resistance means 27 (cf. FIG. 2). The recess may be formed preferably in the casing of the disposable module 2.

Figure 3:
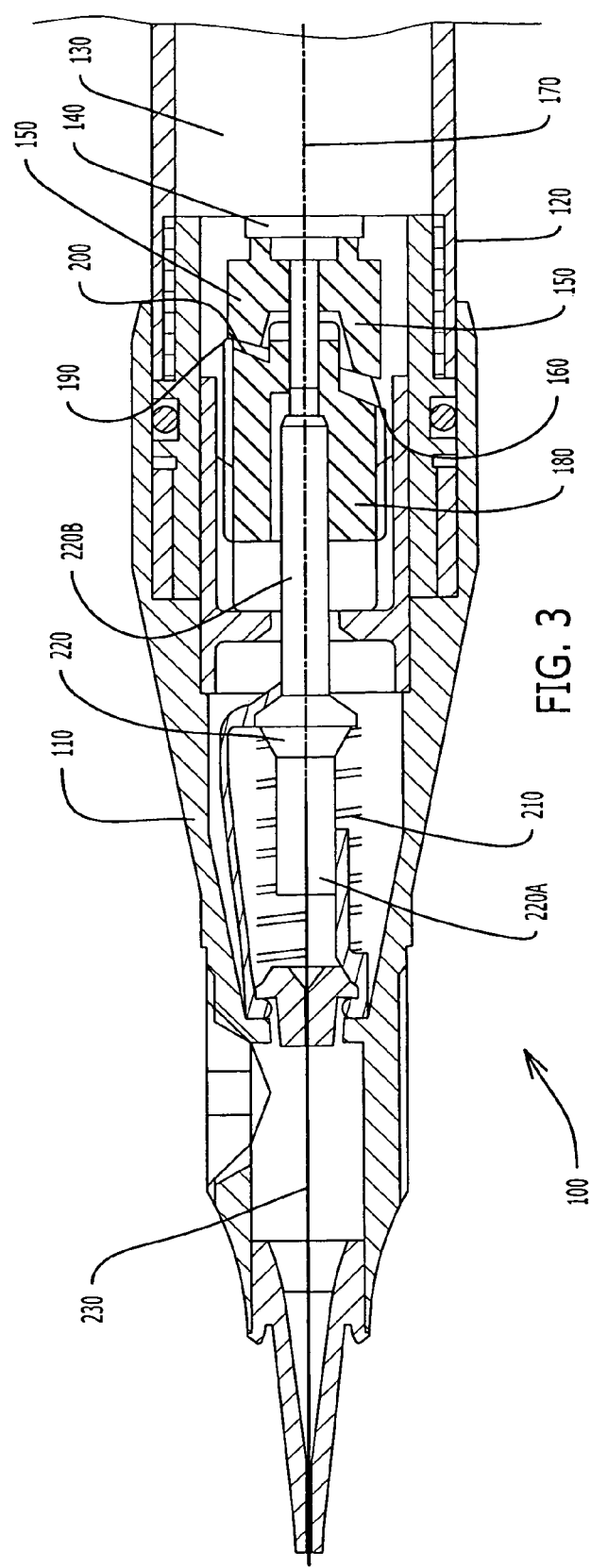
FIG. 3 is a sectional illustration of a front portion of an apparatus for applying tattooing or permanent make-up.

FIG. 3 is a sectional elevation of another apparatus 100 for applying tattooing or permanent make-up by means of a disposable module 110 and a handpiece 120. The handpiece 120 houses a drive comprising a motor 130 and a drive shaft 140. A structural member (first cam member) 150 is mounted on the drive shaft 140 to rotate as the drive shaft 140 itself rotates. At its side remote from the motor 130, the structural member 150 has an oblique surface (first cam surface) 160 which is inclined at an angle other than 90° with respect to the axis 170 of the drive shaft 140.

Another structural member (second cam member) 180 is arranged opposite the structural member 150 and formed with a protrusion (second cam surface) 190 which contacts the oblique surface 160 in a zone along the edge 200. When the structural member 150 rotates, the protrusion 190 is held on the oblique surface 160 by having a spring 210 urge the other structural member 180 in the direction of the structural member 150. The pressure exerted by the spring 210 is introduced into the needle shaft 220 through the other structural member 180, a needle 230 being held in a front portion 220a of the needle shaft 220. The other structural member 180 sits on a rear portion 220b of the needle shaft 220.

The structural member 150 and the other structural member 180 form part of coupling means for inducing the drive motion of the motor 130 and the drive shaft 140 in the needle shaft 220 and the needle 230. The structural member 150 and the other structural member 180 act as conversion means to convert the rotary movements of the drive shaft 140 into reciprocating movements of the needle shaft 220 and the needle 230. The other structural member 180 is arranged in the disposable module 110 and removable together with the same from the handpiece 120. Thus it can be exchanged together with the disposable module. In this manner, the conversion mechanism is formed at least partly in the disposable module 110 and may be severed from the handpiece 120 together with the disposable module.

Rotation of the structural member 150 caused by the motor 130 moves the protrusion 190 in a circular path on the oblique surface 160, while the other structural member 180 is held by the protrusion 190, for instance, by torque resistance means. Upon rotation of the oblique surface 160, the other structural member 180 together the needle shaft 220 fixed to it and the needle 230 are reciprocated in linear motion along the axis 170.

The features of the invention disclosed in the specification above, in the claims and drawing may be significant to implementing the invention in its various embodiments, both individually and in any combination.

What is claimed is:

1. An apparatus for applying a tattoo or permanent make-up, comprising:
a handpiece having a rotary drive,
a detachable needle holding module connected to one end of said handpiece, the detachable needle holding module being disposed on one end of the handpiece and the detachable needle holding module is connected directly to an end portion of the handpiece, said detachable needle holding module including therein a needle shaft, a needle guide having an opening, and a needle disposed in said needle shaft and supported for movement in said needle guide and extending through a needle nozzle opening in the detachable needle holding module, and
a drive mechanism including at least one structural member coupled to said needle shaft to achieve reciprocating movements of said needle, said at least one structural member including a coupler for coupling the rotary drive to said needle shaft,
wherein said coupler comprises a conversion mechanism to convert a rotary drive motion generated by said rotary drive into linear motion of said needle shaft, a portion of the conversion mechanism being disposed in the handpiece and another portion of the conversion mechanism being attached to said detachable needle holding module, said detachable needle holding module and said another portion of the conversion mechanism defining a disposable module and being structured and arranged to be simultaneously removable together in unison from said handpiece,
wherein the coupler further comprises a first coupling member and a second coupling member, wherein the second coupling member is coupled to the rotary drive, and wherein the first coupling member is pressed against a surface of the second coupling member by a retaining element.

2. The apparatus as claimed in claim 1, wherein said conversion mechanism comprises a wobble plate fixed to said rotary drive and a tappet coupled to said needle shaft and urged on a wobbling surface of said wobble plate, said tappet having a torque resistance member attached to a portion of the disposable needle holding module.

3. The apparatus as claimed in claim 1, further comprising a torque resistor constituting part of said conversion mechanism arranged in said detachable needle holding module and being simultaneously removable from said handpiece together with said detachable needle holding module.

4. The apparatus as claimed in claim 1, wherein said retaining element is a bearing and said conversion mechanism includes
an inner race of said bearing fixed to said rotary drive,
a connecting rod pivotally connected to an outer race of said bearing,
a thrust rod pivotally connected to said connecting rod so as to achieve an axial movement thereof, and
a torque resistance member for preventing said outer race from rotating during operation of said rotary drive.

5. The apparatus as claimed in claim 1, wherein said conversion mechanism includes
a first cam member fixed to said rotary drive, said first cam member having a first cam surface inclined to an axis of rotation of said rotary drive, and
a second cam member having a protrusion extending parallel to the axis of rotation of the rotary drive and contacting said first cam surface, said second cam member being retained in said detachable needle holding module so as to be capable of axial movement and being coupled to said needle shaft during operation of said rotary drive.

6. The apparatus of claim 1, wherein the retaining element comprises a spring element.

7. The apparatus of claim 1, wherein the retaining element is arranged in the detachable needle holding module.

8. An apparatus for applying a tattoo or permanent make-up, comprising:
a handpiece having a drive element,
a detachable needle holding module connected to one end of said handpiece, the detachable needle holding module being disposed on one end of the handpiece and the detachable needle holding module is connected directly to an end portion of the handpiece, said detachable needle holding module including therein a needle shaft, a needle guide having an opening, and a needle disposed in said needle shaft and supported for movement in said needle guide and extending through a needle nozzle opening in the detachable needle holding module, and
a drive mechanism including at least one structural member coupled to said needle shaft to achieve reciprocating movements of said needle, said at least one structural member including a coupling mechanism for coupling the drive element to said needle shaft,
wherein said coupling mechanism comprises a conversion mechanism to convert a rotary drive motion generated by said drive element into linear motion of said needle shaft, a portion of the conversion mechanism being disposed in the handpiece and another portion of the conversion mechanism is disposed in said detachable needle holding module, said detachable needle holding module and said another portion of the conversion mechanism defining a disposable module and being structured and arranged to be simultaneously removable together in unison from said handpiece,
wherein the coupling mechanism further comprises a first coupling member and a second coupling member, wherein the second coupling member is coupled to the rotary drive, and wherein the first coupling member is pressed against a surface of the second coupling member by a retaining element.

9. The apparatus as claimed in claim 8, wherein said conversion mechanism comprises a wobble plate fixed to said drive element and a tappet coupled to said needle shaft and urged on a wobbling surface of said wobble plate, said tappet having a torque resistance member attached to a portion of the disposable needle holding module.

10. The apparatus as claimed in claim 8, further comprising a torque resistance mechanism constituting part of said conversion mechanism arranged in said detachable needle holding module and being simultaneously removable from said handpiece together with said detachable needle holding module.

11. The apparatus as claimed in claim 8, wherein said conversion mechanism includes
an inner race of a bearing fixed to said drive element,
a connecting rod pivotally connected to an outer race of said bearing,
a thrust rod pivotally connected to said connecting rod so as to achieve an axial movement thereof, and
a torque resistance mechanism for preventing said outer race from rotating during operation of said drive element.

12. The apparatus as claimed in claim 8, wherein said conversion mechanism includes
 a first cam member fixed to said drive element, said first cam member having a first cam surface inclined to an axis of rotation of said drive element, and
 a second cam member having a protrusion extending parallel to the axis of rotation of the drive element and contacting said first cam surface, said second cam member being retained in said detachable needle holding module so as to be capable of axial movement and being coupled to said needle shaft during operation of said drive element.

13. An apparatus for applying a tattoo or permanent make-up, comprising:
 a handpiece having a drive member,
 a detachable needle holding module connected to one end of said handpiece, the detachable needle holding module being disposed on one end of the handpiece and the detachable needle holding module is connected directly to an end portion of the handpiece, said detachable needle holding module including therein a needle shaft, a needle guide having an opening, and a needle disposed in said needle shaft and supported for movement in said needle guide and extending through a needle nozzle opening in the detachable needle holding module, and
 a drive mechanism including at least one structural member coupled to said needle shaft to achieve reciprocating movements of said needle, said at least one structural member including a coupling member for coupling the drive member to said needle shaft,
 wherein said coupling member comprises a conversion mechanism to convert a rotary drive motion generated by said drive member into linear motion of said needle shaft, a portion of the conversion mechanism being disposed in the handpiece and another portion of the conversion mechanism is disposed in said detachable needle holding module, said detachable needle holding module and said another portion of the conversion mechanism defining a disposable module and being structured and arranged to be simultaneously removable together in unison from said handpiece,
 wherein the coupling member further comprises a first coupling member and a second coupling member, wherein the second coupling member is coupled to the rotary drive, and wherein the first coupling member is pressed against a surface of the second coupling member by a retaining element, and
 further comprising a torque resistance member constituting part of said conversion mechanism arranged in said detachable needle holding module and being removable from said handpiece together with said detachable needle holding module.

14. An apparatus for applying a tattoo or permanent make-up, comprising:
 a handpiece having a drive member,
 a detachable needle holding module connected to one end of said handpiece, the detachable needle holding module being disposed on one end of the handpiece and the detachable needle holding module is connected directly to an end portion of the handpiece, said detachable needle holding module including therein a needle shaft, a needle guide having an opening, and a needle disposed in said needle shaft and supported for movement in said needle guide and extending through a needle nozzle opening in the detachable needle holding module, and
 a drive mechanism including at least one structural member coupled to said needle shaft to achieve reciprocating movements of said needle, said at least one structural member including a coupling member for coupling the drive member to said needle shaft,
 wherein said coupling member comprises a conversion mechanism to convert a rotary drive motion generated by said drive member into linear motion of said needle shaft, a portion of the conversion mechanism being disposed in the handpiece and another portion of the conversion mechanism is disposed in said detachable needle holding module, said detachable needle holding module and said another portion of the conversion mechanism defining a disposable module and being structured and arranged to be simultaneously removable together in unison from said handpiece,
 wherein the coupling member further comprises a first coupling member and a second coupling member, wherein the second coupling member is coupled to the rotary drive, and wherein the first coupling member is pressed against a surface of the second coupling member by a retaining element, and
 wherein said retaining element is a bearing and said conversion member mechanism includes
 an inner race of said bearing fixed to said drive member,
 a connecting rod pivotally connected to an outer race of said bearing,
 a thrust rod pivotally connected to said connecting rod so as to achieve an axial movement thereof, and
 a torque resistance member for preventing said outer race from rotating during operation of said drive member.

15. An apparatus for applying a tattoo or permanent make-up, comprising:
 a handpiece having a drive member,
 a detachable needle holding module connected to one end of said handpiece, the detachable needle holding module being disposed on one end of the handpiece and the detachable needle holding module is connected directly to an end portion of the handpiece, said detachable needle holding module including therein a needle shaft, a needle guide having an opening, and a needle disposed in said needle shaft and supported for movement in said needle guide and extending through a needle nozzle opening in the detachable needle holding module, and
 a drive mechanism including at least one structural member coupled to said needle shaft to achieve reciprocating movements of said needle, said at least one structural member including a coupling member for coupling the drive member to said needle shaft,
 wherein said coupling member comprises a conversion mechanism to convert a rotary drive motion generated by said drive member into linear motion of said needle shaft, a portion of the conversion mechanism being disposed in the handpiece and another portion of the conversion mechanism is disposed in said detachable needle holding module, said detachable needle holding module and said another portion of the conversion mechanism defining a disposable module and being structured and arranged to be simultaneously removable together in unison from said handpiece, and
 wherein said conversion mechanism includes
 a first cam member fixed to said drive member, said first cam member having a first cam surface inclined to an axis of rotation of said drive member, and
 a second cam member having a protrusion extending parallel to the axis of rotation of the drive member, said second cam member being retained in said detachable needle holding module so as to be capable of axial movement and being coupled to said needle shaft during operation of said drive member.

* * * * *